(12) United States Patent
L'Helgoual'ch

(10) Patent No.: US 10,646,106 B2
(45) Date of Patent: May 12, 2020

(54) ENDOSCOPIC DEVICE INTENDED, IN PARTICULAR, FOR A MEDICAL USAGE

(71) Applicant: Guy L'Helgoual'ch, Brest (FR)

(72) Inventor: Guy L'Helgoual'ch, Brest (FR)

(*) Notice: Subject to any disclaimer, the term of this patent is extended or adjusted under 35 U.S.C. 154(b) by 571 days.

(21) Appl. No.: 14/380,348

(22) PCT Filed: Feb. 12, 2013

(86) PCT No.: PCT/EP2013/052758
§ 371 (c)(1),
(2) Date: Aug. 21, 2014

(87) PCT Pub. No.: WO2013/124184
PCT Pub. Date: Aug. 29, 2013

(65) Prior Publication Data
US 2015/0011825 A1    Jan. 8, 2015

(30) Foreign Application Priority Data

Feb. 24, 2012   (FR) ...................................... 12 51711

(51) Int. Cl.
*A61B 1/002*    (2006.01)
*A61B 1/055*    (2006.01)
(Continued)

(52) U.S. Cl.
CPC .......... *A61B 1/002* (2013.01); *A61B 1/00073* (2013.01); *A61B 1/042* (2013.01);
(Continued)

(58) Field of Classification Search
CPC .......... A61B 1/00096; A61B 1/000163; A61B 1/00165; A61B 1/00167; A61B 1/0017; A61B 1/00172; A61B 1/00174; A61B 1/00177; A61B 1/00179; A61B 1/00181; A61B 1/00183; A61B 1/00186;
(Continued)

(56) References Cited

U.S. PATENT DOCUMENTS 4,784,118 A * 11/1988 Fantone ................. A61B 1/002
                                                    359/434
5,093,719 A *  3/1992 Prescott ............... G02B 3/0087
                                                      348/65
(Continued)

FOREIGN PATENT DOCUMENTS

FR      2 899 087 A1   10/2007
WO       00/54033 A1    9/2000
WO    WO 2011/154970 A1   12/2011

OTHER PUBLICATIONS

International Preliminary Report on Patentability dated May 19, 2014 for PCT/EP2013/052758—English Translation.
(Continued)

*Primary Examiner* — Ryan N Henderson
(74) *Attorney, Agent, or Firm* — Knobbe, Martens, Olson & Bear, LLP

(57) ABSTRACT

An endoscopic device includes an optical guide head connfigured to be at least partially inserted into a body or a cavity in order to view or image an object or a site that is poorly accessible to the naked eye. The optical guide head of such an endoscopic device is formed from an optical rod with a refractive index gradient.

10 Claims, 1 Drawing Sheet

Figure 1:
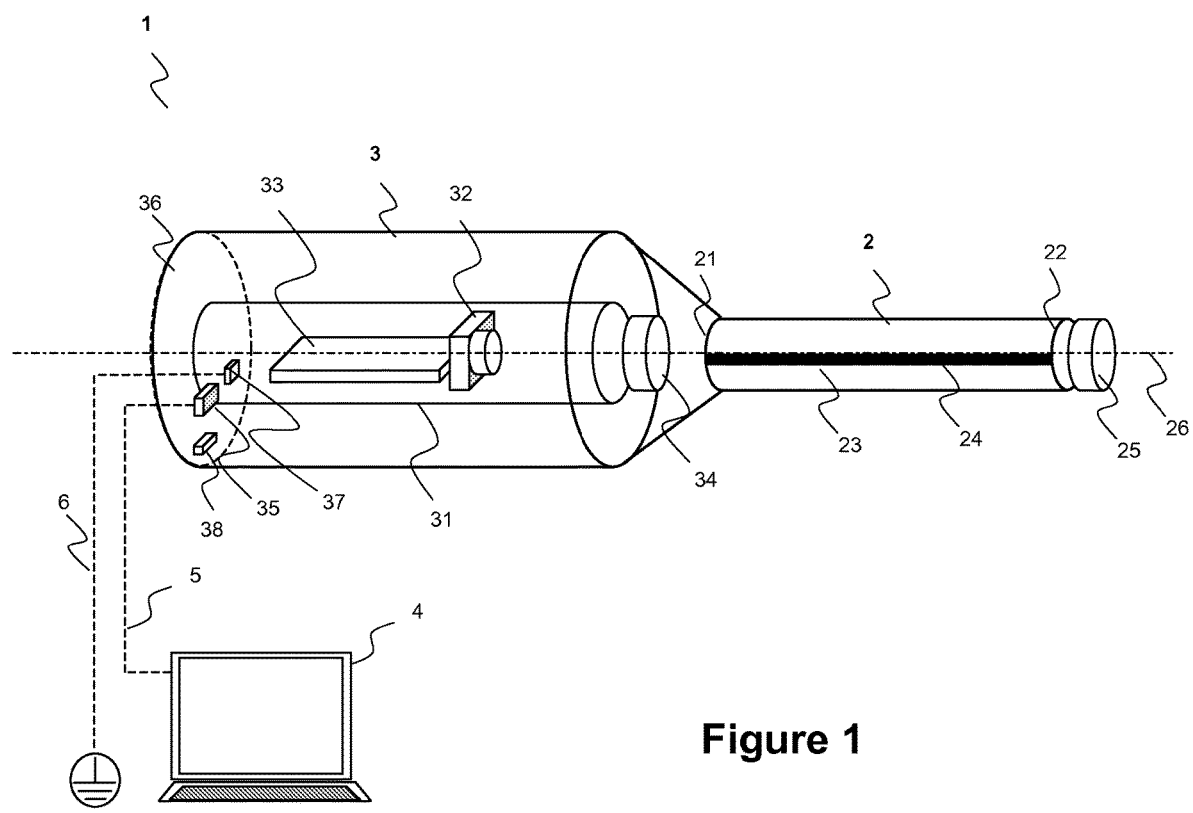

(51) Int. Cl.
*A61B 1/06* (2006.01)
*A61B 1/07* (2006.01)
*G02B 23/24* (2006.01)
*A61B 1/00* (2006.01)
*A61B 1/04* (2006.01)

(52) U.S. Cl.
CPC ............ *A61B 1/055* (2013.01); *A61B 1/0669* (2013.01); *A61B 1/07* (2013.01); *G02B 23/2446* (2013.01)

(58) Field of Classification Search
CPC .............. A61B 1/00188; A61B 1/0019; A61B 1/00193; A61B 1/00195; A61B 1/00197; A61B 1/002; A61B 1/04; A61B 1/042; A61B 1/043; A61B 1/055; A61B 1/06; A61B 1/0607; A61B 1/0615; A61B 1/0623; A61B 1/0638; A61B 1/0646; A61B 1/0653; A61B 1/0661; A61B 1/0669; A61B 1/0676; A61B 1/0684; A61B 1/07; A61B 1/227; A61B 3/10; A61B 3/1005; A61B 3/101; A61B 3/1015; A61B 3/102; A61B 3/1025; A61B 3/103; A61B 3/107; A61B 3/113; A61B 3/117; A61B 3/12; A61B 3/1208; A61B 3/1216; A61B 3/1225; A61B 3/1233; A61B 3/1241; A61B 3/125; A61B 3/13; A61B 3/14; G02B 23/24; G02B 23/2407; G02B 23/2415; G02B 23/2423; G02B 23/2438; G02B 23/2446; G02B 23/2453; G02B 23/2461; G02B 23/2469; G02B 23/26
USPC ....... 600/109–112, 160–181; 348/45, 65–70; 385/117–119; 356/241.1–241.6
See application file for complete search history.

(56) References Cited

U.S. PATENT DOCUMENTS

| | | | |
|---|---|---|---|
| 5,353,792 A | 10/1994 | Luebbers | |
| 5,396,366 A * | 3/1995 | Brown | A61B 1/00165 359/435 |
| 5,457,576 A | 10/1995 | Atkinson | |
| 5,603,687 A * | 2/1997 | Hori | A61B 1/00096 348/45 |
| 5,612,816 A * | 3/1997 | Strahle | A61B 1/00193 351/216 |
| 5,737,013 A * | 4/1998 | Williams | A61B 1/00177 348/66 |
| 5,881,195 A | 3/1999 | Walker | |
| 6,301,043 B1 * | 10/2001 | Lei | G02B 23/2407 359/435 |
| 8,317,689 B1 * | 11/2012 | Remijan | A61B 1/00142 600/112 |
| 9,046,338 B2 * | 6/2015 | Boccara | A61B 5/0066 |
| 2002/0087047 A1 | 7/2002 | Remijan et al. | |
| 2011/0242302 A1 * | 10/2011 | Jacobsen | A61B 1/05 348/68 |

OTHER PUBLICATIONS

International Search Report dated Mar. 7, 2013 for PCT/EP2013/052758.
International Preliminary Report on Patentability dated May 19, 2014 for PCT/EP2013/052758.
Rol et al., "Optical properties of miniaturized endoscopes for ophthalmic use", Optical Engineering, vol. 34, No. 7, pp. 2070-2077, Jul. 1995.

* cited by examiner

ENDOSCOPIC DEVICE INTENDED, IN PARTICULAR, FOR A MEDICAL USAGE

RELATED APPLICATIONS

This application is the U.S. National Phase of International Application No. PCT/EP2013/052758, filed Feb. 12, 2013, designating the U.S. and published in French as WO 2013/124184 on Aug. 29, 2013 which claims the benefit of French Patent Application No. 1251711 filed Feb. 24, 2012.

1. FIELD OF THE INVENTION

The field of the invention is that of endoscopic instruments intended for the exploring and viewing of the interior of organs, conduits or cavities that are inaccessible to the naked eye.

More specifically, the invention relates to an endoscopic device comprising an optical guide head designed to be inserted into a body or a cavity to visualize or magnify an object or a site that is poorly accessible to the human eye.

The invention has numerous applications, inter alia in the field of medical imaging for the internal examination of organs of the human body for diagnostic and/or therapeutic purposes (operational endoscopy) or else in the industrial field for the viewing and checking of internal structures of hollow bodies and mechanical parts.

2. TECHNOLOGICAL BACKGROUND

We shall strive more particularly here below in this document to describe the issues and problems existing in the field of medical imaging and more particularly in the field of ocular imaging (viewing of the internal structures of the eye) which the inventors of the present patent application have faced. The invention is of course not limited to this particular field of application but is of interest for any endoscopy device (or endoscope) that has to cope with similar or proximate issues and problems.

The endoscopic devices used at present to examine the structure of the human eye comprise a rigid invasive part, called an optical guide head, intended to penetrate a patient's organ. This optical guide head is formed generally by a metal tube with an external diameter of some millimeters (for example a stainless-steel tube with an external diameter of 0.9 mm) containing an optical system formed either by a series of optical lenses or by a bundle of optical fibers agglutinated with a cohesion bonder.

Typically, the bundle of optical fibers is connected to an image sensor (such as a video camera) by means of an adapter, the image sensor itself being connected to a display screen. The bundle of optical fibers enables the images of the observed object to be conveyed to the image sensor, after these images are shaped, retransmits them in real time to the display screen.

The metal tube is also provided with a system of illumination by optical fibers used to convey the light from an external pack, provided with a light source, up to the observation zone.

A gripping means is fixedly joined to the metal tube to facilitate the handling of the endoscope and spatial position-finding.

This type of endoscope nevertheless has numerous drawbacks.

To ensure the rigidity of the optical guide head when it is inserted into the patient's organ, the metal tube must have a certain thickness. This limits the quantity of light reaching the image sensor. Since the amount of detail captured by the image sensor is thus limited, the quality of the images rendered on the screen is relatively lowered.

In addition, the optical guide heads, whether they are formed by optical lenses or optical fibers, are technically complex and costly to manufacture.

Indeed, a guide head using optical lenses requires a very precise assembly of a plurality of optical lenses in a metal tube having limited dimensions owing to the requirements of miniaturization (the internal diameter of the tube could sometimes be as little as a few hundreds of micrometers), to form the optical objective of the endoscope. The lenses are particularly fragile optical components.

In addition, the cable of the guide head generally comprises a bundle of optical fibers of great length (capable of reaching up to several meters) giving rise to non-negligible losses of light. The optical fiber cable is substantially sized and does not enable easy handling of the endoscope.

Finally, to avoid any risk of infection of the patient, it is necessary to have aseptic endoscopic equipment available. To this end, the endoscopes are sterilized before each use (for example by autoclave sterilization), often leading to premature ageing of the endoscopes. This includes not only the optical guide head in direct contact with the patient and the gripping means but also the optical fiber cables. These features make the autoclave operations difficult and a source of breakage and deterioration of the system.

There is therefore a need for a low-cost endoscopic device that is simple to use offering guarantees in terms of health safety and enabling the rendering of high-quality images.

3. GOALS OF THE INVENTION

The invention, in at least one embodiment, is aimed especially at overcoming these different drawbacks of the prior art.

More specifically, it is a goal of at least one embodiment of the invention to provide a technique that can be used to obtain a low-cost endoscopic device that is very simple to manufacture and assemble.

At least one embodiment of the invention is also aimed at providing a technique of this kind that improves the quality of the images rendered by the endoscopic device as compared with the images rendered by the endoscopic devices of the prior art.

In other words, one of the goals of this technique, in at least one embodiment, is to make the use of endoscopic devices, for example in the context of medical imaging, more easy.

It is another goal of at least one embodiment of the invention to provide a technique of this kind that overcomes the constraints related to the premature ageing of the components due to the sterilizing operations.

4. SUMMARY OF THE INVENTION

At least one particular embodiment of the invention proposes an endoscopic device comprising an optical guide head intended to be inserted, at least in part, into a body or a cavity in order to view a given object that is inaccessible to the naked eye, said optical guide head being constituted by an optical bar with refraction index gradient.

The term "optical bar with index gradient" is understood to mean a solid optical component (as compared with a tube) of any unspecified section, made out of a material having mechanical, geometrical and optical characteristics that enable the performance of:

the function of an invasive endoscopic rod that gets inserted into a body or a cavity inaccessible to the naked eye;

the function of an optical waveguide enabling the transportation of light rays coming from the object to be viewed and the formation of images in a predefined image focal plane.

Whereas in the prior-art endoscopic devices, the optical guide head requires two distinct elements, one to act as an invasive part (rigid metal tube) and the other to act as an optical guide (optical lenses or optical fibers), the optical guide head according to the invention uses one and the same element to simultaneously perform both these functions.

Since the optical bar already benefits from the mechanical characteristics of an invasive endoscopic rod, it becomes unnecessary to provide a rigid metal tube in the optical guide head as in the prior-art endoscopes, and the entire diameter of the optical bar (and therefore of the optical guide head) can be used to guide light from its distal end up to its proximal end. Since it is no longer limited by the thickness of the metal tube, the sensing field of the optical head is increased, enabling a greater quantity of light to be guided through the optical guide head. In addition, because of the optical bar, it is no longer necessary to use an optical fiber bundle of great length. The solution of the invention therefore offers users the advantage of having available an endoscopic device rendering images of far greater quality than those rendered by the prior-art devices (there is no loss related to the presence of optical fibers, nor is there any limitation of the sensing field because of the metal tube), thus facilitating the interpretation of the images.

Since the complex operations of mounting optical lenses or optical fibers in a metal tube to obtain an optical guide head are no longer necessary, the cost of mounting and manufacturing such a device is diminished.

Thus, advantageously, the material and profile of the index gradient are chosen so that the optical bar fulfils the above-mentioned two functions.

According to one advantageous characteristic, the endoscopic device comprises an image sensor and the optical bar with refraction index gradient is such that it comprises a proximal end and a distal end, each treated so as to form an image on the image sensor from light rays coming from the object to be viewed.

It is no longer necessary to use a series of optical lenses or a bundle of optical fibers to form the image to be viewed on the image sensor since the shape of the ends of the optical bar associated with the refraction index gradient already fulfils this function.

Advantageously, at least one of said ends known as the proximal end and distal end belongs to the list comprising:
 a flat end;
 an aspherical end;
 an diffractive Fresnel lens.
 This list is not exhaustive.

In particular, an aspherical lens has the advantage of preventing the appearance of optical aberrations.

Advantageously, the endoscopic device comprises a sensing field expanding optical lens laid out at the distal end of the optical bar.

This widens the sensing field of the optical bar, a major parameter especially in the context of eye surgery for example, which generally requires the use of an optical guide head of small diameter (0.9 mm for example).

According to one advantageous characteristic, the optical bar with index gradient comprises at least one longitudinal rail capable of receiving an optical illumination fiber to illuminate the object to be viewed in proximity to the distal end of the optical bar.

The presence of an optical illuminating fiber in the longitudinal rail prompts the appearance of a peripheral spot in the circular image. This peripheral spot can serve as an image orientation reference marker for the user.

According to a first variant of an embodiment, the device comprises a means for gripping (or gripping means) so that said means for gripping and the optical bar with index gradient form a single-piece unit.

This alternative embodiment thus offers any user the advantage of a "turnkey" endoscopic device that is simple to use and capable of one-time use. Indeed, the single-piece unit can be designed so that it is made out of a material enabling one-time use of said single-piece unit.

The term "one-time use" is understood to mean that the mode of manufacture of the single-piece unit is adapted so that this single-piece unit can be used only once. The use of an endoscopic device with one-time use makes it possible especially to ensure a high level of hygiene for said device.

According to a second alternative embodiment, the device comprises a means for gripping mechanically coupled with the optical bar with index gradient via reversible mechanical coupling means.

This embodiment thus offers any user the possibility of assembling the endoscopic device or dismantling it into two distinct parts through the presence of the reversible mechanical coupling means.

It is possible to use interchangeable optical guide heads, for example in the context of a particular use requiring a change of diameter of the optical bar or again of the image-taking optics inherent in the optical bar.

Again, such an embodiment enables the user to sterilize the means for gripping, the optical bar (which can be dismantled from the means for gripping) being the element sensitive to high temperatures. This therefore enables a one-time use of the optical guide head, ensuring a high level of hygiene for this optical head.

The reversible mechanical coupling means belong to the group comprising:
 clip-on coupling means;
 screw-in coupling means;
 plug-in coupling means;
 male/female linkage coupling means;
 bayonet coupling means.
 This list is not exhaustive.

According to one advantageous characteristic, the image sensor is an image sensor embedded in the means for gripping.

In this way, the users have available an endoscopic device with an embedded sensor. It can be advantageous to plan for a wireless communications port to transmit the images of the object viewed towards a display screen. The absence of a wire link makes the surgical operations easier.

Advantageously, the device comprises a focal-distance adapting optical system positioned in proximity to the embedded image sensor, between the optical bar with index gradient and the embedded image sensor.

This makes it possible to image the object to be viewed in the image sensor with greater precision.

The focal-distance adapting optical system belongs to the group comprising:
 an optical lens with fixed focal distance;
 a series of detachable lenses with variable focal distance;
 a liquid-based or liquid-crystal-based adaptive optical system.

The invention thus provides for the possibility of implementing either a fixed lens or a series of detachable of lenses or an adaptive optical system before the image sensor. The fixed lens is used to adjust the focal distance of the optical system constituted by the optical bar. The adaptive optical system implements the following by modulation of a refraction index of the liquid or liquid crystal:

a mechanism for variable fine-tuning of the sharpness of the image in the focal plane of the image sensor;

a mechanism for adjusting a variable focal distance.

Thus, the endoscopic device herein offers the possibility of adapting the image-taking optical system of the optical guide head.

Advantageously, the means for gripping furthermore comprises at least one embedded light source and/or an autonomous electrical supply.

Since there is no longer any need to provide for a supply of light and/or a supply of electricity to make the endoscopy device operational, the handling of the endoscopy device is all the more facilitated.

Advantageously, the optical bar with index gradient is made out of an optically transparent material belonging to the group comprising:

polymethyl methacrylate (PMMA);
polycarbonate;
glass.

It must be noted that this list is not exhaustive.

Advantageously, the optical bar with index gradient is coated with an opaque protective film.

Such a protective film prevents parasitic light rays ("noise") from getting added to the light rays coming from the object to be viewed, for example during contact of the optical bar with wet cloth, which could result in a deterioration of the quality of the images rendered.

5. LIST OF FIGURES

Figure 2:
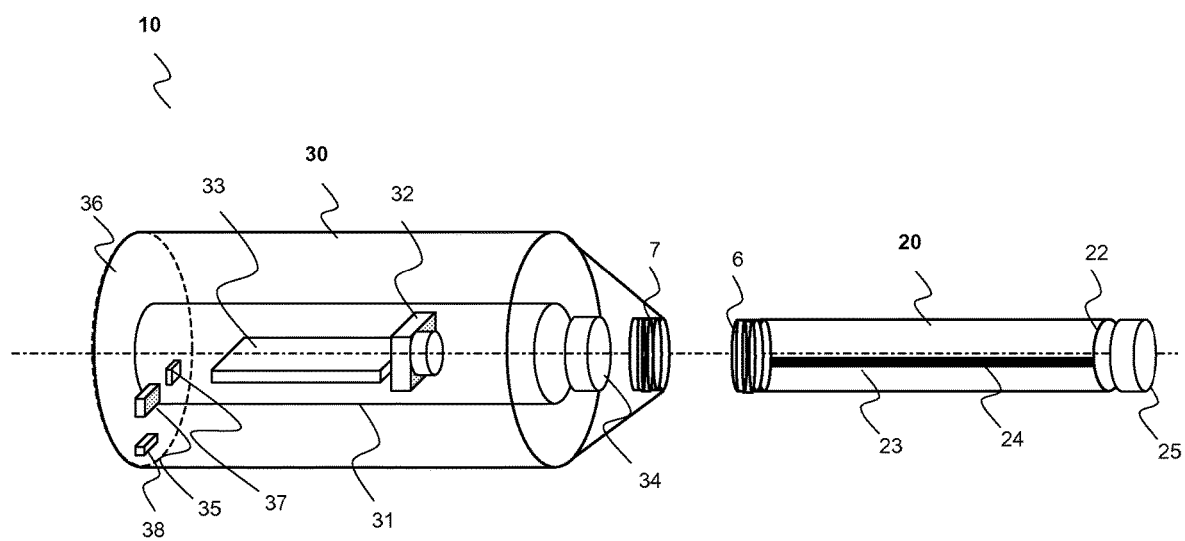

Other features and advantages of the invention shall appear from the following description, given by way of an indicative and non-exhaustive example and from the appended drawings, of which:

FIG. 1 presents an overall view of an endoscopic device according to a first embodiment of the invention;

FIG. 2 presents an overall view of an endoscopic device according to a second embodiment of the invention.

6. DETAILED DESCRIPTION

In all the figures of the present document, the identical elements are designated by a same numerical reference.

FIG. 1 represents an overall view of an endoscopic device 1 according to a first embodiment of the invention. The endoscopic device comprises a sleeve-shaped grip or handle 3 and an optical guide head 2.

The optical guide head 2 is constituted by a circular-sectioned optical bar, made out of a material with a radial refractive index gradient. The term "material with radial refraction index gradient" is understood to mean a material having a non-homogenous refraction index decreasing with the distance along the optical axis 26 of the bar up to the external periphery of this bar. This gives an effect of optical convergence of the light rays entering the optical bar 2.

By way of a purely illustrative example, the optical bar 2 is made out of PMMA (polymethyl methacrylate) with a refraction index gradient having a fourth-order polynomial profile and a core refraction index of 1.49. It is cylindrical and has, for example, a length of 35 mm and a diameter of about 0.9 mm. Other dimensions, index profiles and materials are of course possible without departing from the framework of the invention. Eye surgery operations, for example, generally require the use of an optical guide head of small diameter, possibly ranging from 0.5 mm to 1.5 mm, the length of the optical head then having to be adapted so as to fulfill the optical waveguide function.

The index gradient profile of the optical bar 2 can be obtained for example by ion doping, drawing, specific cooling of an optical material or any other technique well known to those skilled in the art, such as those commonly used for the manufacture of telecom optical fibers for example. The proximal end 21 and the distal end 22 are each machined on their external surface so as to obtain two distinct profiles, so that the light rays emanating from the viewed object pass through the optical bar with index gradient 2, from the distal end 22, and form an image thereof in the focal plane of the image sensor 32. The proximal end 21 and distal end 22 are therefore treated so as to participate, with the refraction index gradient of the bar, in the effect of optical convergence of the light rays to form images in the focal plane of the image sensor 32.

Should the optical bar 2 be obtained by molding, the profile of the surfaces of the proximal end 21 and distal end 21 as well as the dimensions of the bar are defined by the imprint of the mould. It is enough indeed to adjust the dimensions of the mould to obtain the desired surface profiles and dimensions. Through these particular optical and mechanical characteristics, the optical bar 2 according to the invention constitutes a unique element which acts as an optical wave guide, which is essential for transporting the light rays coming from the viewed object up to the image sensor 32 and as an invasive rod that is rigid enough to be able to be introduced without breaking, for example into a patient's eye or into any other organ. Whereas the prior-art endoscopes make use of two distinct elements to form an optical element, one to carry out the optical wave guide function (with optical fibers or optical lenses) and the other to carry out the invasive rod function (as a metal tube), the endoscopic device 1 of the invention requires only one element—the optical bar with an index gradient 2—to fulfill both these functions.

It must be noted that those skilled in the art will adapt the material as well as the index gradient profile to be used for the optical bar 2 so that the above-mentioned conditions are met. In general, the optical bar possesses optical characteristics sufficient to enable the imaging of the object visualized on an image sensor (and thus fulfill the function of a wave guide) and to be rigid enough to be capable of being inserted into an organ (and thus fulfill the invasive rod function).

The following examples, given by way of purely illustrative and non-exhaustive examples, present some of the materials of which the optical bar of the invention can be constituted: polycarbonate, organic glass or mineral glass, etc. The optical bar 2 also comprises a longitudinal rail 23 which can be used to house an optical illuminating fiber 24 illuminating the object to be viewed at a proximate point of the distal end 22. The optical fiber 24 is supplied with light from the exterior by means of a supply pack (not illustrated), this pack being equipped for example with a tungsten lamp.

The grip 3 has dimensions suited to easy holding of the endoscopic device 1 and for the integration of video capture elements. More specifically, the grip 3 comprises an embedded video camera 31, comprising firstly an image sensor 32, for example of a CCD (charge-coupled device) type made with CMOS (complementary metal oxide semiconductor) technology, and secondly an electronic board 33 for managing images picked up by the image sensor and for commanding certain functions of the endoscopic device 1.

The light rays coming from the filmed object illuminate the image sensor 32 via the optical bar 2 which fulfils the function of an optical objective. The image sensor 32 converts the light rays (photons) that it receives into electrical signals (electric charges). For each illuminated pixel, an electrical signal is digitized, then analyzed by an integrated circuit (not illustrated) in the electronic board. Each image sensed by the image sensor 32 is then sent, in the form of a video display signal, towards a display screen 4.

An endoscopic device 1 can be equipped with a man/machine interface, for example situated on the rear face 36 of the grip, comprising:
- a power switch 37, for example of an on/off type, to power on or power off the endoscopic device 1;
- a wire communications port 35, for example of a USB (universal serial bus) type to receive a cable 5 providing for the output of the video display signal towards a display screen 4;
- a power port 38 for the electrical power supply of the endoscopic device 1 via a power cable 6.

In one alternative embodiment, it can be planned to use only one port on the man/machine interface 36, fulfilling the functions of both video display signal output and electrical power supply for the endoscopic device 1.

According to another alternative embodiment, the endoscopic device 1 could be electrically powered by means of an autonomous electrical power supply unit such as a battery or rechargeable cells for example. In this case, the grip 3 comprises a housing (not shown) of a size adapted to the integration of said battery and said rechargeable cells. The output of the video display signal could be provided in this case by wireless transmission means (not shown), for example of a WiFi or 4G type, integrated into the man/machine interface 36 and intended for communication with integrated wireless reception means integrated into the display screen 4. The grip can advantageously comprise another housing (not shown) of a size adapted to integrating an illuminating lamp, for example of a LED (light-emitting diode) type to supply the optical illuminating fiber 34 with light. Thus, in this alternative embodiment, no electrical power supply cable, light supply cable or display video signal transmission cable is henceforth necessary. This makes the endoscopic device 1 firstly easier to handle and, secondly, totally autonomous.

The embodiment described here in FIG. 1 illustrates an endoscopic device integrating an embedded video camera 31. It is clear that many other embodiments of the invention can be envisaged. It is possible especially to provide for a grip having a longitudinal housing (not shown), the dimensions of which are suited to housing an external video camera within the endoscopic device 1. This variant has the advantage whereby it is possible to use a higher-quality camera and discard, after use, only the single-piece unit comprising the optical bar 2 and the grip 3, the video camera being subsequently reutilizable for other operations. In this case, the video camera should itself have a man/machine interface such as the interface 36 of the grip described further above (alternative modes of implementation of this interface, described in detail further above, could also be applied to this embodiment).

Optionally, the man/machine interface 36 can also be equipped with a digital display screen on which the images of the object viewed with the endoscopic device 1 are displayed.

The grip device 3 furthermore comprises a focal-distance adapting optical system 34 placed before the embedded image sensor 32, between the optical bar 2 and the embedded image sensor 32. According to one particular implementation, this focal-distance adapting optical system 34 can be an integral part of the video camera 31. This optical system is aimed at higher-precision imaging of the object filmed with the endoscopic device on the image sensor. It can be a fixed lens, a series of mechanical detachable lenses or an adaptive optical system such as a liquid lens or a liquid-crystal lens. The fixed lens can be used to adjust the focal distance of the optical system constituted by the optical bar 2. The adaptive optical system makes it possible, under the effect of at least one element control signal, to adjust the focal distance of the optical system and/or to fine-tune the sharpness of the images by modulation of a refraction index of the liquid or of the liquid crystal.

In the embodiment presented here, the optical bar 2 and the grip 3 are made out of a same material and form a single-piece unit. This single-piece unit can be obtained by various methods of manufacture widely described in the literature. By way of a purely illustrative example, the single-piece unit 2, 3 can be made out of PMMA according to a standard technique of molding enabling industrial-scale manufacture in large volumes.

A single-piece endoscopic device can also be made by fixedly and definitively joining the optical bar 2 and the grip 3, the optical bar 2 being made according to a standard technique of manufacture similar to the one used for making optical fibers and the grip 3 being made according to a standard molding technique. Naturally, the grip 3 can be made, in this case, out of a material that is different from the material used to manufacture the optical bar 2.

PMMA is a low-cost material. The invention makes it possible to obtain a low-cost single-piece endoscopic device that is very simple to manufacture. Thus, when this device integrates low-cost components such as the embedded video camera for example, the invention enables a one-time use of the endoscopic device. This can prove to be particularly advantageous in the context of surgical operations, especially after each use, since the endoscopic device can be discarded, thus preventing any problems related to sterilizing operations.

Finally, the optical bar 2 herein comprises an optical lens 25 for magnifying the sensing field positioned on its distal end 22 to widen the sensing field of the optical bar 2. The optical bar 2 can furthermore comprise a protective film (not illustrated in the figure) positioned on the external periphery of this bar to prevent the picking up of parasitic light rays ("noise") by the image sensor 32.

It can also prove to be advantageous to have available an endoscopic device that can be assembled/disassembled as illustrated here below with reference to FIG. 2.

FIG. 2 shows an overall view of a particular embodiment of the endoscopic device 10 in which it is dismantled. It comprises as in the device 1 of FIG. 1, an optical bar 20 forming an optical guide head and a sleeve-shaped grip 30. This embodiment advantageously makes it possible to implement an endoscopic device with interchangeable optical heads.

For example, one and the same surgical operation can necessitate the use of several optical bars of different diameters: an optical bar with a given diameter can be very well suited to a particular step and unsuited to another step. In addition, the fact of having interchangeable optical bars means that it is possible to sterilize only the optical bars if the grip comprises high-quality optical and electronic components and/or components sensitive to sterilizing temperatures. Finally, when replacing the optical bar by another, it is possible to modify the image-taking optical system. It is possible for example to plan to replace a first optical bar by a second optical bar for which the convergence power of the light rays is higher and to which a prismatic lens has been added, on the invasive side, to make the shooting ("image taking") axis vary by a given angle.

The grip 30 is mechanically coupled with the optical bar via reversible mechanical coupling means 6, 7. More specifically, the optical bar 20 comprises a threaded part 6 at its proximal end that is complementary to a threaded aperture 7 made in the grip 30 and making it possible, by mechanical screwing, to couple and fixedly join the optical bar 20 to the grip 30.

The geometrical dimensions of said mechanical coupling means such as the diameter and the thread pitch, are characteristics which those skilled in the art are capable of defining according to the desired geometrical dimensions of the optical bar and of the means for gripping, enabling precise and easy fastening of these two elements.

Other coupling means can of course be implemented without departing from the framework of the invention, for example clip-on coupling means, bayonet coupling means (advantageous for their precision of mechanical alignment and their speed of installation), plug-in (or insertion) coupling means, etc.

Such an embodiment provides an endoscope that is simple to assemble.

The two embodiments described here above are intended for medical endoscopy and especially ocular endoscopy. It is clear however that it can easily be adapted to many other applications without departing from the framework of the invention.

What is claimed is:

1. An endoscopic device comprising:
    a grip including an image sensor therein;
    an optical guide head configured to be inserted, at least in part, into a body or a cavity in order to view a given object that is inaccessible by direct view of a physician, wherein the optical guide head comprises a single organic glass-based optical rod,
    wherein the single organic glass-based optical rod is formed of organic glass continuously from a proximal end to a distal end of the optical rod;
    wherein the single organic-based optical rod has an outer diameter in a range of 0.5 mm to 1.5 mm, and a length of about 35 mm from the proximal end to the distal end, and a refraction index gradient with a polynomial profile;
    wherein the proximal end of the single organic glass-based optical rod is attached to the grip; and
    wherein the single organic glass-based optical rod is configured to form an image on the image sensor from light rays coming from the object to be viewed;
    an illumination fiber disposed within a longitudinal rail formed in the single organic glass-based optical rod; and
    an optical lens disposed at the distal end of the single organic glass-based optical rod, the optical lens configured to magnify the image of the object onto the single organic class-based optical rod.

2. The endoscopic device according to claim 1, wherein at least one of said proximal end and said distal end belongs to the list comprising:
    a flat end;
    an aspherical end; and
    a diffractive Fresnel end.

3. The endoscopic device according to claim 1, wherein the optical lens comprises a sensing field expanding optical lens.

4. The endoscopic device according to claim 1, wherein the grip is configured to allow a user to grip the endoscopic device and wherein the grip and the single organic glass-based optical rod with index gradient form a single-piece unit.

5. The endoscopic device according to claim 1, wherein the image sensor is embedded in the grip.

6. The endoscopic device according to claim 5, comprising a focal-distance adapting optical system positioned in proximity to the embedded image sensor, between the single organic glass-based optical rod with index gradient and the embedded image sensor.

7. The endoscopic device according to claim 6, wherein the focal-distance adapting optical system belongs to the group comprising:
    an optical lens with fixed focal distance;
    a series of detachable lenses with variable focal distance; and
    a liquid-based or liquid-crystal-based adaptive optical system.

8. The endoscopic device according to claim 4, wherein the grip further comprises at least one embedded light source and/or an autonomous electrical supply.

9. The endoscopic device according to claim 1, wherein the single organic glass-based optical rod with index gradient is made out of an optically transparent material belonging to the group comprising:
    polymethyl methacrylate (PMMA);
    polycarbonate; and
    glass.

10. The endoscopic device according to claim 1, wherein the single organic glass-based optical rod with index gradient is coated with an opaque protective film.

* * * * *